(12) United States Patent
Treu

(10) Patent No.: US 12,178,950 B2
(45) Date of Patent: Dec. 31, 2024

(54) TREATMENT FLUID MULTI-STREAM BLOOD WARMER

(71) Applicant: NxStage Medical, Inc., Lawrence, MA (US)

(72) Inventor: Dennis M. Treu, Castle Rock, CO (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 18/224,127

(22) Filed: Jul. 20, 2023

(65) Prior Publication Data

US 2023/0355852 A1 Nov. 9, 2023

Related U.S. Application Data

(62) Division of application No. 16/467,680, filed as application No. PCT/US2017/066431 on Dec. 14, 2017, now Pat. No. 11,752,249.

(Continued)

(51) Int. Cl.
*A61M 1/36* (2006.01)
*A61M 1/16* (2006.01)
(Continued)

(52) U.S. Cl.
CPC .......... *A61M 1/36* (2013.01); *A61M 1/1601* (2014.02); *A61M 1/1664* (2014.02);
(Continued)

(58) Field of Classification Search
CPC .............. A61M 1/1601; A61M 1/1664; A61M 1/3403; A61M 1/36; A61M 1/3623;
(Continued)

(56) References Cited

U.S. PATENT DOCUMENTS 4,728,433 A 3/1988 Buck et al.
4,894,150 A 1/1990 Schurek et al.
(Continued)

FOREIGN PATENT DOCUMENTS

CN 104383619 B 3/2015
DE 202016002935 U1 5/2016
(Continued)

OTHER PUBLICATIONS

Extended European Search Report dated Jul. 10, 2020 for European Patent Application No. 17880416.7.
(Continued)

*Primary Examiner* — John Kim
(74) *Attorney, Agent, or Firm* — Potomac Law Group, PLLC

(57) ABSTRACT

The disclosed subject matter relates to extracorporeal blood processing or other processing of fluids. A blood treatment system treats blood with multiple fluids and performs fluid balancing on a patient's blood compartment. Multiple streams influence the patient temperature but only a subset of the fluids are dynamically temperature regulated. The system regulates a temperature of the flow, for example, of dialysate in order to regulate the return temperature of blood, in such a way that the temperature effect of the multiple streams is compensated.

6 Claims, 8 Drawing Sheets

Related U.S. Application Data

(60) Provisional application No. 62/434,075, filed on Dec. 14, 2016.

(51) Int. Cl.
*A61M 1/34* (2006.01)
*A61M 5/44* (2006.01)

(52) U.S. Cl.
CPC ........ *A61M 1/3403* (2014.02); *A61M 1/3623* (2022.05); *A61M 5/44* (2013.01); *A61M 2205/3331* (2013.01); *A61M 2205/3334* (2013.01); *A61M 2205/3368* (2013.01); *A61M 2205/366* (2013.01)

(58) Field of Classification Search
CPC ............ A61M 5/44; A61M 2205/3331; A61M 2205/3334; A61M 2205/3368; A61M 2205/366
See application file for complete search history.

(56) References Cited

U.S. PATENT DOCUMENTS

| | | |
|---|---|---|
| 5,344,568 A | 9/1994 | Kitaevich et al. |
| 5,836,908 A | 11/1998 | Beden et al. |
| 6,284,131 B1 | 9/2001 | Hogard et al. |
| 2013/0020237 A1 | 1/2013 | Wilt et al. |
| 2015/0204733 A1 | 7/2015 | Newell et al. |
| 2016/0058933 A1 | 3/2016 | Ballantyne et al. |

FOREIGN PATENT DOCUMENTS

| | | |
|---|---|---|
| EP | 2848269 A1 | 3/2015 |
| WO | 2010027437 A2 | 3/2010 |
| WO | 2017062923 A1 | 4/2017 |

OTHER PUBLICATIONS

International Search Report and Written Opinion for PCT/US2017/066431 issued May 8, 2018.

TREATMENT FLUID MULTI-STREAM BLOOD WARMER

CROSS-REFERENCE TO RELATED APPLICATIONS

This application is a divisional of U.S. application Ser. No. 16/467,680 filed Jun. 7, 2019, now U.S. Pat. No. 11,752,249, which is a U.S. national stage filing under 35 U.S.C. § 371 of International Application No. PCT/US2017/066431 filed Dec. 14, 2017, which claims the benefit of U.S. Provisional Application No. 62/434,075, filed Dec. 14, 2016, all of which are hereby incorporated by reference in their entireties.

BACKGROUND

A basic function of many extra corporeal blood treatment systems (ECBT systems), including hemodialysis, hemofiltration, hemodiafiltration, apheresis systems, etc., is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter or dialysis are equal. To provide for a desired differential between the net quantity removed/added, the inflow and outflow rates can be controlled to produce a net difference. This may be provided by regulating the relative flow rates provided by ingoing and outgoing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump in an attempt to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

Another function provided by extracorporeal blood treatment systems is the maintenance of blood temperature of the patient under treatment. Such extracorporeal blood treatments fall into a variety of categories ranging from blood oxygenation and therapeutic hypothermia to renal replacement therapies such as hemodialysis (HD). In extracorporeal blood treatments, such as HD, blood is pumped from a patient through a blood circuit and through a treatment device, such as a dialyzer. Toxins and electrolyte exchange across a dialyzer membrane to exchange with a treatment fluid. The exchange causes the removal of waste products in the blood and excess water. A substantial volume of the patient's blood may pass through an extracorporeal blood treatment system during the course of a treatment such that any heat transfer to or from the blood can upset the patient's body temperature.

SUMMARY

The disclosed subject matter described in this disclosure includes approaches to volumetric fluid balance using multiple volumetric or fixed-displacement pumps to control inflows and outflows from an extracorporeal circuit that have corresponding pump rates synchronized relative to each other to assure balanced flow rates. Techniques for maintaining patient blood temperature during treatment with multiple fluid streams while ensuring safe handling of blood are addressed.

In certain systems, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flow that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through predilution, post-dilution, citrate infusion, and reverse ultrafiltration streams may be balanced against the net ultrafiltration stream to achieve a target net ultrafiltration rate. The subject matter described in this disclosure provides machine configurations that support one or more therapy fluid flows synchronized with the effluent fluid flow from the extracorporeal circuit to achieve accurate fluid balance and the warming of fluid in such systems.

The disclosed subject matter includes several different system configurations that support one or more therapy fluid inlet flows balanced with the effluent flow. In embodiments, reliable flow balance is obtained by synchronizing the pump flows by various control mechanisms. The temperature of the blood is maintained by adding heat to a subset of the treatment fluid streams such that heat is transferred to the blood without creating a local temperature rise that might adversely affect the blood and so as to warm blood to a predefined temperature of the blood returned to the patient. To this end, the temperature of blood in a venous line (blood return temperature) connected for return flow of blood to the patient is continuously monitored and used for negative feedback control. The set point of the blood return temperature can be established based on an estimate of the heat transfer from/to the environment between the point of the blood return temperature measurement and the patient blood access (e.g., fistula needle, central line, or dual needle access).

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1:
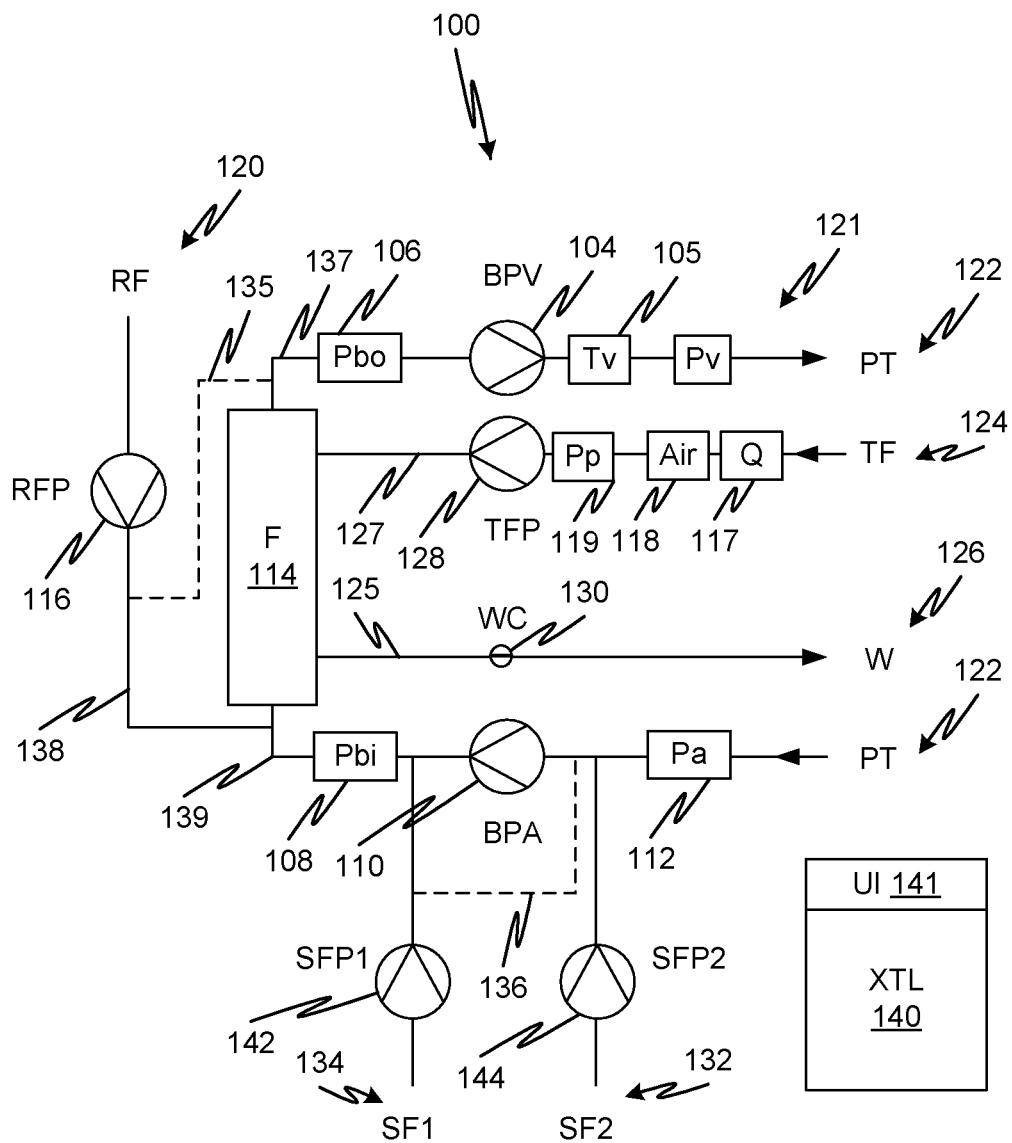
FIG. 1 shows a treatment fluid multi-stream blood treatment system that regulates the flow of blood relative to a treatment fluid to generate a cumulative target ratio of fluid drawn or infused into a patient over the course of a treatment while maintaining a blood temperature.

FIG. 1 shows a blood treatment system 100 that regulates the flow of fluid in a fluid circuit 121 that includes an arterial blood line 139, a venous blood line 137, a fresh treatment fluid line 127 and a waste treatment fluid line 125. In particular, the blood treatment system 100 regulates the flow of blood relative to a treatment fluid to generate a cumulative target ratio of fluid drawn or infused into a patient over the course of a treatment or drawn or returned to a priming fluid source/sink, respectively. The net flow of fluid into or out of a patient (priming fluid source/sink—hereafter any reference to "patient" and/or "blood" with reference to a synchronization mode or synchronization operation may be replaced by priming fluid and/or a combination source and sink thereof, because the synchronization mode/operation mode discussed herein can be done during priming with a recirculating or single-pass priming operation as well as during a treatment, as will be evident to the skilled artisan), at any given time, is determined by a then-instant difference between the volume of blood pumped from a treatment device 114 (labeled F for filter, for example a dialyzer, a common embodiment) to the volume pumped into the treatment device 114. Blood is pumped into the treatment device 114 by an arterial blood pump 110 and pumped from the treatment device 114 by a venous blood pump 104. The illustrated configuration is common for dialysis systems, and may include all the typical incidents thereof, but differs specifically in that there are two blood pumps: the arterial blood pump 110 and the venous blood pump 104.

During a treatment mode and also in embodiments of a synchronization mode, blood is pumped to and from a patient access 122. In other embodiments synchronization may be done instead with a priming fluid. During priming operations, the patient access or priming connector(s) may be connected to priming fluid source, sink, or recirculating container instead. Thus, 122 may be considered generally to represent a patient access connected to a patient, in which case the circulating fluid is blood, or 122 may be considered to represent a priming fluid source, sink, or recirculating container, in which case, the circulating fluid is priming fluid.

Control and sensing are provided by a controller 140 which may be of any form but typically some type of programmable digital controller, for example, an embedded computer. A treatment fluid is pumped from a treatment fluid source 124 through an air detector 118 through the treatment device 114, past a waste line clamp 130, to the drain 126 (indicated by W for waste). Drain 126 may be a drain of a plumbing system or a collection container or any other device for disposal of waste treatment fluid. Treatment fluid 124 may be dialysate, replacement fluid, or any other medicament.

A replacement fluid 120 may be pumped into the arterial blood line 139 or the venous blood line 137 through a replacement fluid line 135 or 138, respectively (or both) for predilution, post-dilution or a combination of both. In alternative embodiments, the dilution may occur at a midpoint of the treatment device 114, for example by using a two smaller units of a treatment device 114 that provides a junction between them or by means of a special structure of the treatment device 114 that provides for mid-dilution. The treatment device 114 may be adapted for a variety of types of blood treatment that require balancing flows into and out of a fluid circuit, including, but not limited to, dialysis, hemofiltration, hemodiafiltration, apheresis, adsorption, or hemoperfusion. These treatment modalities apply to all of the disclosed embodiments including those originally disclosed in the claims. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the blood line 139 upstream of the arterial blood pump 110. In embodiments, each pump contributing to flow balance may have a pressure sensor up stream of it to ensure that pressure compensated control of its speed can be provided. For example, an additional treatment fluid pump pressure sensor 119 may be provided. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122. The controller 140 receives signals from each of the arterial pressure sensor 112, blood inlet pressure sensor 108, blood outlet pressure sensor 106, and venous blood pressure sensor 102 as well as an air sensor 118 (also referred to as an air detector) that is positioned to detect air in the fresh treatment fluid line 127. The controller 140 is also connected to control each of the arterial blood pump 110, venous blood pump 104, replacement fluid pump 116, supplemental fluid pump 142, and supplemental fluid pump 144, as well the waste line clamp 130. Note that the waste line clamp 130 could be replaced by any type of valve that selectively halts or permits flow or another pump.

In alternative configurations, instead of treatment fluid pump 128 and waste line clamp 130 being used to halt flow as described below, a waste fluid pump may be provided in the position of waste line clamp 130, which can halt flow by halting rotation. In any of the embodiments, including the present and further embodiments to be described below or described above, any element identified as a line or fluid line (or fluid circuit) could be any type of flow channel including interconnected tubes including pumping tube segments, channels formed in a cartridge (as a pattern of troughs sealed by an overlying welded film), a pattern-welded pair of weldable sheets, a laminated stack of elements that defines flow channels, or any other device that guides the flow of fluid. Any element identified as a pump may be any type of pump or actuator that is volumetric aka, positive displacement type. Peristaltic pump is a type of a positive displacement pump. Such embodiments of lines and fluid lines or fluid circuits may be disposable or otherwise replaceable components that engage pumps, sensors, and actuators of a treatment machine that includes such pumps, sensors, and actuators as identified in the embodiments. Such a machine may be illustrated schematically in the drawings, but not necessarily as a separate component, for example a pump indicated by a single element may include a pump actuator, e.g., a rotor, that works together with a pump tubing segment of a fluid circuit, while both are indicated by a pump symbol schematically in the drawing. Similarly, sensors and clamps are not illustrated separately in all the drawings. Such a machine may be embodied in multiple separate components and may be generally described as having a receiving adapter to allow the connection of a disposable fluid circuit.

The term, receiving adapter, or similar term is an abstraction that may cover all the various mechanisms that permit the operative association between a permanent device and a disposable or replaceable component which together form one of the apparatuses disclosed or claimed. This applies to all the disclosed and claimed embodiments. For example, the drawings described above and below illustrate a system which, when considering that portions are replaceable, indicate the presence of a blood circuit receiving adapter and a medicament (treatment fluid, dialysate, or similar fluid) receiving adapter. The fluid circuits (including blood circuits) may include treatment components as well as portions that engage with sensors and actuators. Again, these comments apply to all embodiments.

Any element identified as a pressure sensor may be a combination of a fluid circuit portion such as a pressure pod or drip chamber and an electronic transducer such as a strain gauge or displacement encoder connected to an element such as a diaphragm that registers pressure. The foregoing elements are well known classes of devices and further elaboration is not needed to permit the skilled reader to develop the details of working embodiments of the described subject matter. Fluids may be supplied from containers such as bags or inline fluid generators such as used in dialysis clinics.

In a treatment operation of blood treatment system 100, arterial blood pump 110 and venous blood pump 104 pump blood or priming fluid in the directions indicated by the respective arrowhead of each pump symbol. They pump at rates controlled by the controller 140 to approximately balance (equivalently, "equalize") the flow of blood in the arterial blood line 139 against the flow of blood in the venous blood line 137 such that a net take-off of fluid (ultrafiltrate) or a net infusion of fluid takes place (which may be called negative ultrafiltrate). The instantaneous rate of ultrafiltration refers to net loss of fluid by the patient and negative ultrafiltration refers to net gain of fluid by the patient. This is achieved through control of the total displaced volume by the arterial pump 110 relative to the venous pump 104. The ultrafiltrate may be established by a predetermined ratio of the flow rates of the arterial 110 and venous 104 pumps if the transfer is spread uniformly over the treatment interval or the net ultrafiltrate may be established in a discontinuous manner by varying the ratio of the flow rates of the arterial 110 and venous 104 pumps to achieve a cumulative ultrafiltrate. Thus, ultrafiltrate volume is established by the total volume transported by the venous pump 104 minus the total volume transported by the arterial pump 110 over the course of a treatment. Ultrafiltrate rate may identify the instantaneous difference between the rates of the venous 104 and arterial 110 pumps.

The controller 140 may be programmed to ensure that the net volume of ultrafiltrate or infused fluid meets a prescribed target which may be stored by the controller 140. The pumping speeds required to achieve commanded flow rates may be determined by the controller 140 using data stored by the controller such as look up tables or formulas. A commanded flow rate refers to the operational property (e.g., shaft speed of a peristaltic pump) that is under direct control of the controller which corresponds more or less accurately to a flow rate, conditions that may vary from those used to establish a transfer function defining the relationship between the operational property and an actual flow rate produced by it. The conditions may include manufacturing variability such as pumping tube segment and fluid line diameter, material properties of the pumping tube segment, pump lubrication, as well as factors that change due to operation history and storage such as distortions, material creep, etc. The ratio of flow rate to pump speed may be presented by stored look-up table data to indicate target pump speeds by a relationship between pressure difference and flow rate.

Treatment fluid 124 is pumped by fresh treatment fluid pump 128 at a predefined rate stored in the controller 140, which rate may be selected to correspond to the blood flow rate. The replacement fluid 120 may be pumped at a rate controlled by the controller 140 by controlling the commanded rate of replacement fluid pump 116. The supplemental fluid 134 may be pumped at a rate controlled by the controller 140 by controlling the commanded rate of supplemental fluid pump 142. The supplemental fluid 132 may be pumped at a rate controlled by the controller 140 by controlling the commanded rate of supplemental fluid pump 144. Any of the replacement fluid 120, supplemental fluid 134, or supplemental fluid 132 are optional and may or may not be included, along with the respective lines and pumps, in alternative embodiments.

Valves or pinch clamps identified anywhere in the current patent application may be of any type. For example, flexible membranes closed over cartridge-embedded ports, electrically actuated pinch clamps employing linear actuators such as solenoid plungers or stepper motor actuators may be used. The particular type of valve mechanism does not limit the disclosed subject matter. Line 136 is present to indicate that in alternative embodiments, the supplemental fluids may enter the arterial blood line 139 upstream or downstream of the arterial blood pump 110.

The return temperature of blood is continuously controlled and maintained by the controller 140 in response to a venous return temperature indicated by a venous return temperature sensor 105. Venous return temperature sensor 105 is positioned and configured to detect the temperature of blood in the venous line and output a corresponding signal to the controller. To control the venous return temperature, the controller 140 regulates the heat output (or if a net cooling is required the refrigeration level) of a thermal regulator 117 that deposits or withdraws heat to or from the treatment fluid in the fresh treatment fluid line 127. The thermal regulator 117 may be a fluid warmer such as a direct contact thermoelectric heater. Alternatively it may be a radiant heater that minimizes the creation of induced electrical current in fluid lines. The thermal regulator 117 may also provide heat and cooling effect or only cooling effect. For example, it may include a thermoelectric cooler such as a thermopile or peltier cooler or it may be vapor compression machine. The examples are not limiting of the invention and any of them as well as others may be combined or substituted to provide alternative embodiments of a device to regulate the temperature of fluid in fresh treatment fluid line 127. All the sensors and actuators identified above may be connected to the controller 140 either by wired or wireless signal connection or through final power drives.

As indicated above, in any of the embodiments, the fluid balance (net ultrafiltrate volume) resulting from the flows to and from a patient is understood to accrue over a period of time. Thus, although in the embodiments, the controller is described as controlling pumping rates to achieve a fluid balance, optionally offset by a net transfer of fluid to or from the patient (net ultrafiltrate volume), it is understood that the pumping rates need not be constant, define a constant ratio over time, or even define a smoothly varying ratio over time. Since the ultimate goal is to control the total loss or gain of fluid from a patient (net ultrafiltrate volume), pumping rates can establish a variety of rates over time such that the cumulative effect is the target ultrafiltrate volume at the end of the treatment. Rates may be constant or vary step-wise, smoothly, and may result in a temporary gain of fluid by the patient during a portion of a treatment interval and net loss during another portion to achieve a total gain or loss for the entire treatment. For another example, the entire fluid gain or loss can be confined to a single part of the treatment interval. The controller may also limit estimated ultrafiltrate so that overall balance does not exceed a certain volume at a given time. A rate of ultrafiltration may also, or alternatively, be limited by the controller.

Figure 2A:
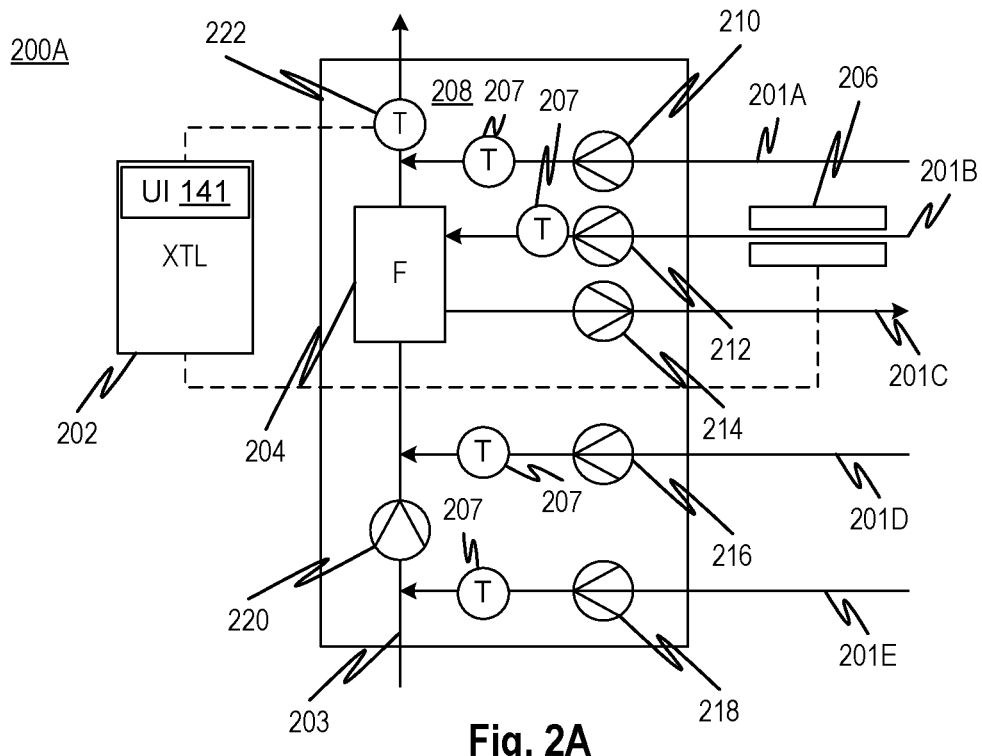
FIG. 2A shows a simplified schematic of a multiple treatment fluid stream system that actively regulates temperatures of at least one stream and includes a controller and treatment device for blood, according to embodiments of the disclosed subject matter.

Referring to FIG. 2A, a blood treatment system 200A has a blood treatment machine 208 which engages with a (preferably disposable) fluid circuit that includes a blood line 203 and treatment fluid lines 201A-201E. Blood is pumped by a blood pump 220. For example, the blood pump may be a peristaltic pump. Fluid pumps 210, 212, 214, 216, and 218 engage with treatment fluid lines 201A-201E, respectively to pump treatment fluids in and out of the fluid circuit. Specifically, for example, a treatment fluid conveyed by treatment fluid line 201A may be a post-dilution fluid, drug, or other medicament, which flows directly and is admixed with blood after the blood flows through a treatment device 204 which may also be part of the fluid circuit. Another treatment fluid may flow through treatment fluid line 201B, pumped by fluid pump 212, into the treatment device 204 and out through treatment fluid line 201C, pumped by treatment fluid pump 214. The difference in flow rates of the treatment fluid pump 212 and treatment fluid pump 214 determines a net rate of addition or loss of fluid to or from the pump. Thus, in this embodiment, the fluid balance of the patient will be determined and controlled by regulating the relative speeds of treatment fluid pump 212 and treatment fluid pump 214.

The treatment device 204 transfers heat to or from the treatment fluid circulating through treatment fluid line 201B and treatment fluid line 201C. The treatment fluid line 201B has a temperature regulator 206 to warm or cool, depending on whether the blood is to be heated or cooled. The temperature regulator may be of any of the types of fluid warmers or refrigerators used for temperature regulation. Preferably it is thermostatically regulated to limit the temperature of fluid leaving it to a predefined range. The power output of the temperature regulator 206 is controllable by the controller 202 which is connected to receive a temperature signal from the blood return temperature sensor 222 indicating the temperature of blood returning to the patient through blood line 203. The controller generates an error input from a difference between the blood return temperature and a predetermined value. It regulates the power output of the temperature regulator 206, for example by negative feedback control. The latter may be achieved by a digital proportional, integral, proportional-integral, or proportional-integral-differential algorithm, for example. The controller may be configured to limit the temperature at which a treatment fluid contacts blood to a predefined range of temperature. For example, the fluid may be limited to the range 30-42 C at all times and between 28-46 C for any time interval greater than 30 seconds. Temperature sensors may be provided on each of the treatment fluid lines to permit the controller to generate an alarm, reduce a rate of heating or cooling of a medicament, and/or reduce or halt the flow of treatment fluids if a range or range per time interval is exceeded.

Another treatment fluid may be conveyed by treatment fluid line 201D may be a pre-dilution fluid, drug, or other medicament, which flows directly and is admixed with blood before the blood flows through the treatment device 204 and after the blood pump 220. The rate of flow through treatment fluid line 201D is regulated by the treatment fluid pump 216. Another treatment fluid may be conveyed by treatment fluid line 201E may be a pre-dilution fluid, drug, or other medicament, which flows directly and is admixed with blood before the blood flows through the treatment device 204 and after the blood pump 220. The rate of flow through treatment fluid line 201E is regulated by the treatment fluid pump 216 whose speed is controlled by the controller 202.

In FIG. 2A as well as FIGS. 2B, 3A, and 3B, 207 indicates a temperature sensor that detects a respective fluid temperature that affects the blood return temperature. Temperature sensor 207 may be a contact type sensor that contacts the fluid channel or blood channel. An example of a contact type sensor is described in Patent Publication US20150204733 to Newell, et al. Other types of contact or wetted temperature sensors may also be used such as RFIDs, thermistors, or any type of temperature sensor able to generate a signal indicating temperature. As discussed herein, the various blood return temperature control algorithms rely on one or more temperatures and the acquisition of these temperatures may be done by any suitable means including by any of a variety of particular locations of the sensors with respect to fluid-conveying channels.

Figure 2B:
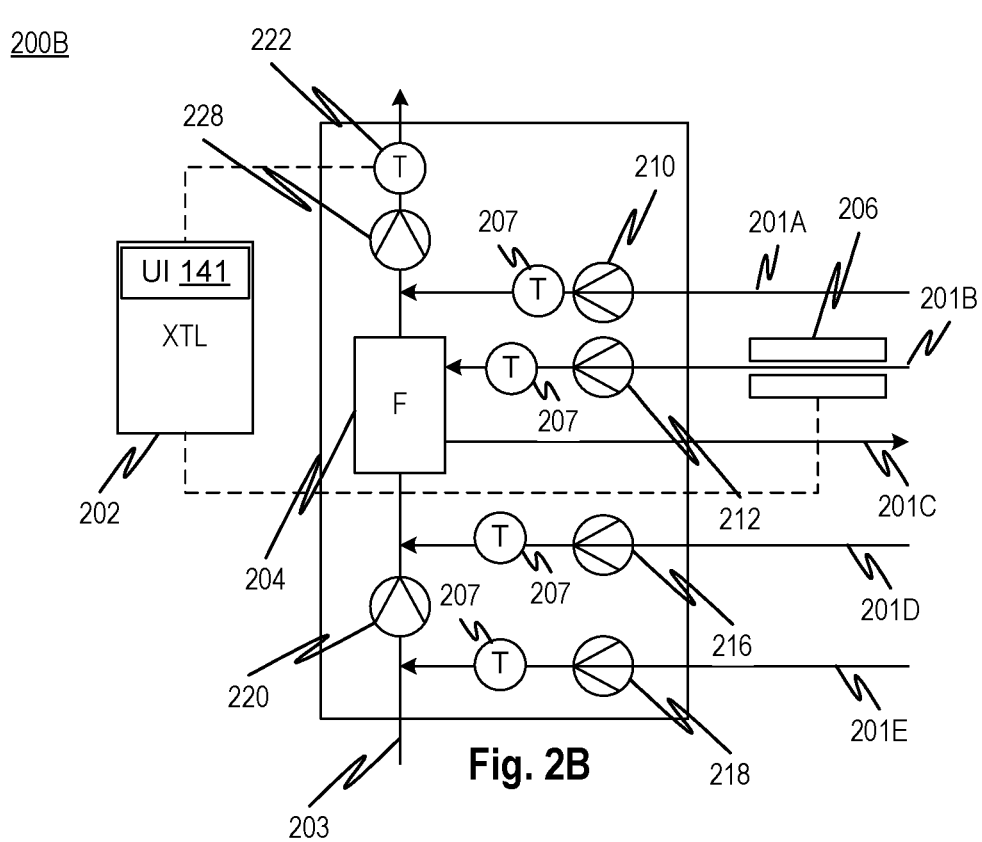
FIG. 2B shows a simplified schematic of a multiple treatment fluid stream system that actively regulates temperatures of at least one stream and includes a controller and treatment device for blood, according to further embodiments of the disclosed subject matter in which fluid balancing is performed in an alternative method and system from that of FIG. 2A.

FIG. 2B shows a simplified schematic of a multiple treatment fluid stream system that actively regulates temperatures of at least one stream and includes a controller and treatment device for blood, according to further embodiments of the disclosed subject matter in which fluid balancing is performed in an alternative method and system from that of FIG. 2A. Referring now to FIG. 2B, the flow balance employs an arterial blood pump 220 and a venous blood pump 228 whose relative pumping speeds determines the rate of ultrafiltration. In the present embodiment, a single treatment fluid pump 212 is used. The control method of FIG. 4 may be used to regulate the power of temperature regulator 206. In other respects the embodiment of FIG. 2B is the same as the embodiment of FIG. 2A so the corresponding description is not repeated.

It should be clear to those of skill in the art of extracorporeal blood treatment systems, from the foregoing description, that the contribution of thermal energy to blood in either of the systems 200A and 200B depends on a combination of admixing of all the treatment fluids entering the system through treatment fluid lines 201A-201E as well as heat transfer between the blood and non-blood compartments of the treatment device 204 which in part determines the exchange of thermal energy between blood and the treatment fluid carried in treatment fluid lines 201B and 201C.

Figure 4:
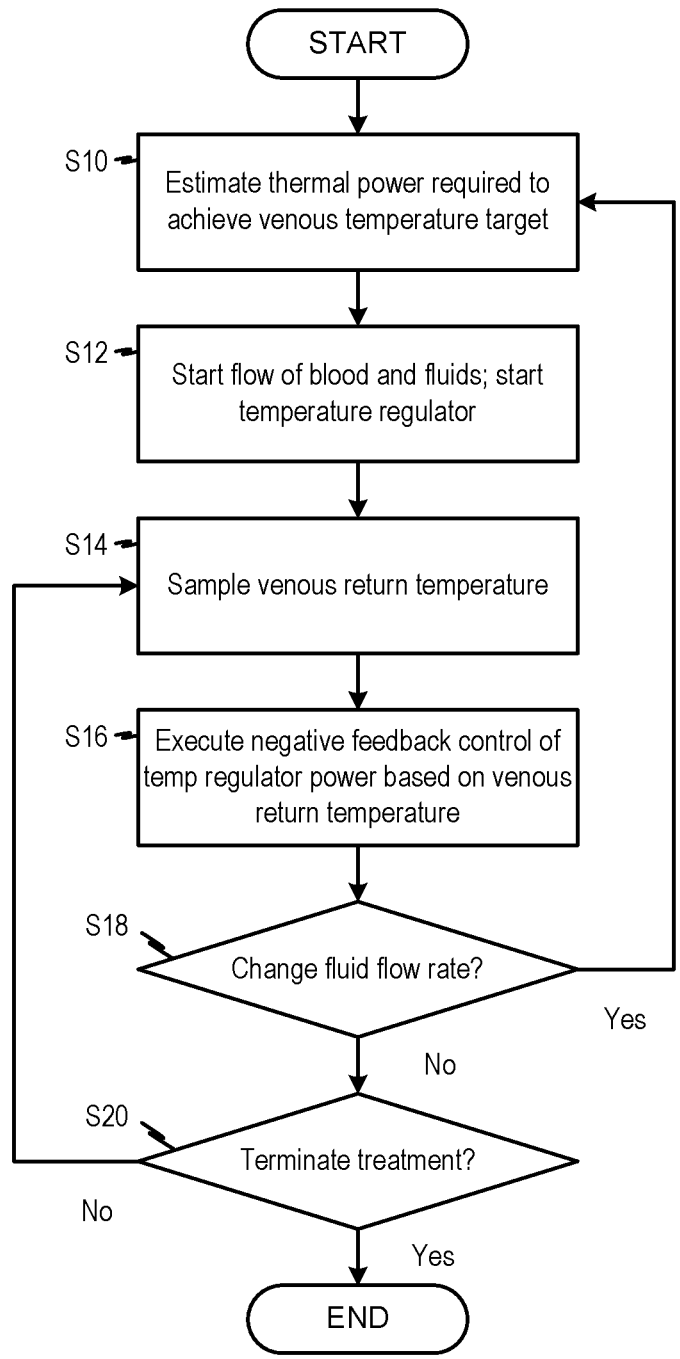
FIG. 4 shows a flow chart defining a controller-implemented method of regulating venous return temperature in the presence of multiple fluids that affect the temperature as shown in the systems of FIGS. 2A and 2B, according to embodiments of the disclosed subject matter.

Referring now to FIG. 4, a flow chart shows a controller-implemented method of regulating venous return temperature in the presence of multiple fluids that affect the temperature as shown in the systems 200A and 200B, according to embodiments of the disclosed subject matter. The procedure starts at S10 with estimating the thermal power output of the temperature regulator 206 to achieve a predefined blood return temperature of the blood as indicated by the blood return temperature sensor 222. This estimate may be standardized based on standard environment temperature or by data entered by a user through a user interface indicating estimated temperature of the treatment fluids carried respectively by the treatment fluid lines 201B and 201C and a predefined target magnitude of the blood return temperature which is stored by the controller either permanently as part of its programming or via a prescription. The initial power required may also be stored as determined by a previous operation such as prior treatments which are controlled according to the present procedure for example. The estimation may factor-in, using a heat transfer model, the initial flow rates of the treatment fluids and blood. A mass balance can be done initially to calculate the blood flow rate at each stage of the blood treatment process, illustrated schematically in FIG. 7.

The mass balance for the first two stages of admixing are given by $$m_{B,2} = m_{B,1} + m_{F,1} \quad (1)$$

$$m_{B,3} = m_{B,2} + m_{F,2} \quad (2)$$

where $m_{B,i}$ is the mass flow rate of blood at the ith stage and $m_{F,j}$ is the mass flow rate of jth treatment fluid at the jth stage. The mass flow of blood after the blood treatment device includes a net ultrafiltration rate equal to the difference between the inflowing and outflowing rates of the third treatment fluid. As indicated below, there is also a pressure-gradient driven convection between blood and treatment fluid compartments but this does not cause a net transfer of fluid between the two compartments so the mass flow of blood remains unaffected by this process.

$$m_{B,4} = m_{F,4} - m_{F,3} + m_{B,3} \quad (3)$$

The mass balance for the final stage of admixing is given by equation 4.

$$m_{B,5} = m_{B,4} + m_{F,1} \quad (4)$$

It will be clear to those of skill in the art that the above mass flow balance pertains to the exemplary system and that other types of systems would involve different algorithms and account for different effects. The example is not intended to be limit the scope of the teachings of the present disclosure. The same applies to the following thermal energy balance discussion.

Figure 7:
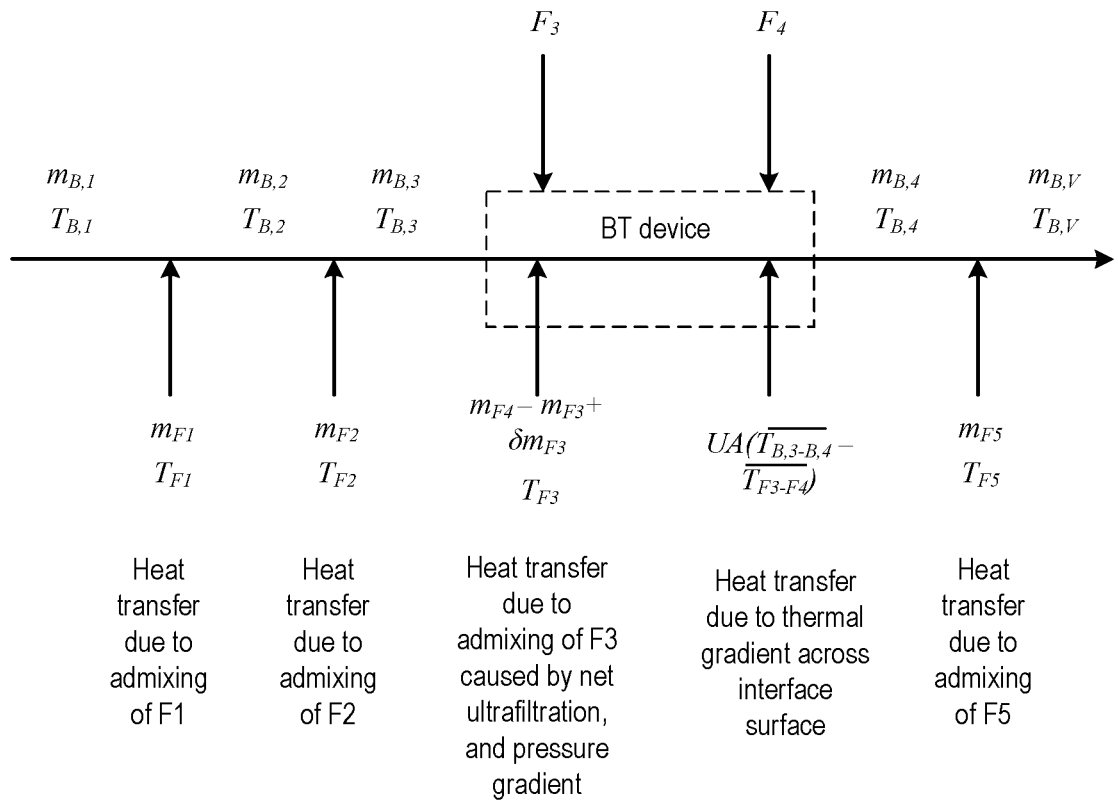
FIG. 7 is a schematic diagram of the flow rates involved in the heat and mass balance of the blood treatment according to any of the embodiments according to a specific example illustrating a method according to any of the disclosed embodiments.

The energy balances for the flow circuit depicted in FIG. 7 may be applied backwards, proceeding from the target blood return temperature $T_V$ to calculate the blood temperature $T_{B,4}$ at the inlet to the junction where the fifth treatment fluid F5 flow is admixed with flowing blood, given by equation 6 by solving for $T_{B,4}$ from the energy balance of equation 5.

$$m_{B,4} c_B (T_V - T_{B,4}) + m_{F5} c_{F5} (T_V - T_{F5}) = 0 \quad (4)$$

$$T_{B,4} = \frac{m_{F5}c_{F5}(T_V - T_{F5}) + m_{B,4}c_B T_V}{m_{B,4}c_B} \quad \text{-continued} \quad (5)$$

Where $c_B$ is the specific heat of blood, $T_{Fi}$ is the ith treatment fluid temperature, $c_{Fi}$ is the ith treatment fluid specific heat, and $T_V$ is the venous blood temperature.

The temperature of blood at the blood treatment device inlet $T_{B,3}$ is calculated from $T_{B,1}$ by the admixing equation 6.

$$T_{B,3} = \frac{m_{B,1}c_B T_{B,1} + m_{F1}c_{F1}T_{F1} + m_{F2}c_{F2}T_{F2}}{m_{B,1}c_B + m_{F1}c_{F1} + m_{F2}c_{F2}} \quad (6)$$

Figure 8:
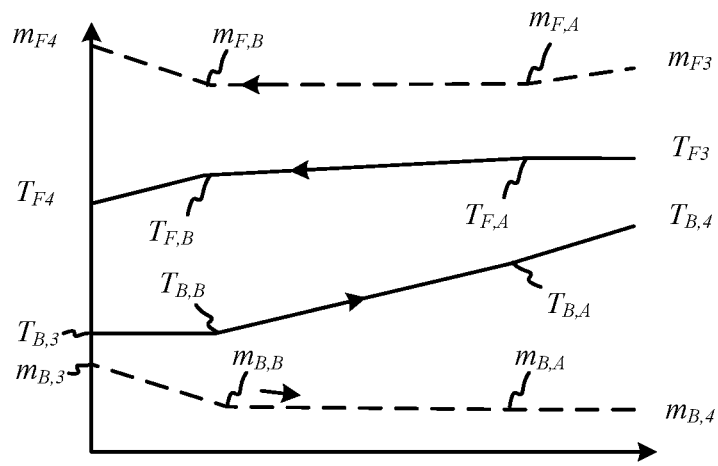
FIG. 8 illustrates temperature and flow changes in an exemplary model of a blood treatment device according to embodiments of the disclosed subject matter.

Referring to FIG. 8, a common type of blood treatment, dialysis, is assumed for the sake of discussing temperature changes for an example. The approach can be modified to suit different types of treatments such as hemofiltration or hemodiafiltration and other types of blood treatments. During dialysis, the ultrafiltration causes a net flow of fluid from the blood to the treatment fluid compartment of the dialyzer causing a gain in mass volume between $m_{F3}$ and $m_{F4}$ with a concomitant loss if mass volume between $m_{B,3}$ and $m_{B,4}$. Note that the flow directions are indicated by the arrows. Because of the change in pressure of blood flowing through the blood treatment device, there may be a net transfer of fluid from blood compartment to the treatment fluid compartment which does not affect the blood temperature but does reduce the temperature of the treatment fluid while simultaneously there is a net gain in temperature of the blood. After a certain point, because of decreasing pressure in the blood compartment as blood flows through, at a later point in the blood treatment device, there may be an offsetting flow from the treatment fluid compartment to the blood. As a result, the mass flow of blood reaches a minimum of $m_{B,A}$ and then rises to $m_{B,4}$, while the mass flow of treatment fluid initially drops and then a minimum of $m_{F,A}$ and then rises to $m_{F4}$. The changes and relative magnitudes are not to scale. There is also a heat gain by convection across the membrane and near the blood outlet there is additional heat added by admixing of treatment fluid causing additional temperature rise of the blood.

Dialyzers are complex heat exchangers and are difficult to model. Even the film coefficient on the surface of the membranes is effected by mass transport across the membrane. Practical ways to estimate the temperature rise due to heat transfer from admixing and thermal convection include an empirical function or a lookup table that show the inlet temperature difference $T_{F3}-T_{B,3}$ for a given blood flow rate, treatment flow rate, and ultrafiltration rate. Such devices allow the estimation of $(T_{F3}-T_{B,3})=F(UF, m_{F3}, m_{B,3})$, where UF is the fraction of the blood flow rate that is withdrawn into the treatment fluid compartment as ultrafiltrate. Then $T_{F3}$ can calculated and the power required to raise the initial temperature $T_{F,in}$ of treatment fluid F3 prior to heating with temperature regulator 206 can be calculated from $Q=m_{F3}c_{F3}(T_{F3}-T_{F,in})$ giving an estimate as indicated in S10.

At S12, the flow of blood and fluids is started and the temperature regulator 206 operated with the estimated power rate. At S14, the blood return temperature is sampled and an error calculated from it based on a stored target blood return temperature to adjust the power of the temperature regulator 206 using a feedback control algorithm at S16. At S18, the controller determines whether the fluid flow rates or blood flow rate have been changed since the previous pass through S18. If one of them has, by a respective predefined magnitude, then control reverts to S10 to estimate the power output for the temperature regulator 206. The change of conditions may include any of those parameters used for the function described relative to S10, including a change in ultrafiltration rate. If it is determined that the flow conditions are constant, then at S20, it is determined whether the treatment has been terminated, if not, control reverts to S14, otherwise the active control of the temperature regulator 206 is terminated.

Figure 3A:
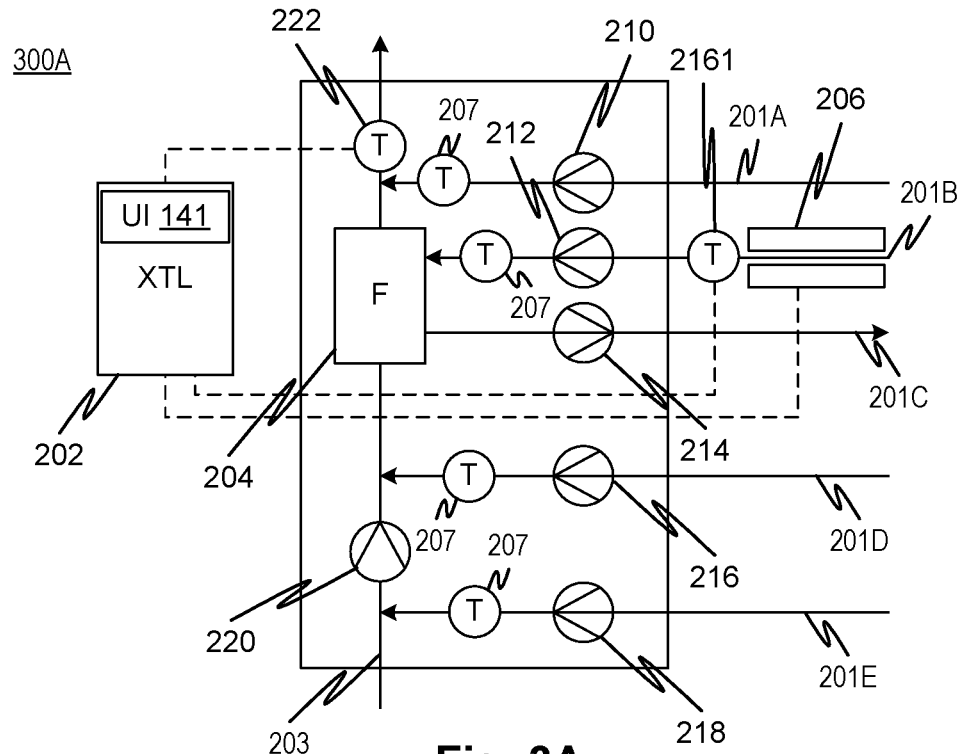
FIG. 3A shows a simplified schematic of a multiple treatment fluid stream system that actively regulates temperatures of at least one stream and includes a controller and treatment device for blood, according to embodiments of the disclosed subject matter in which fluid balancing is performed in a method and system like that of FIG. 2A and a partial feedforward method and system are used for temperature regulation.

FIG. 3A shows a simplified schematic of a multiple treatment fluid stream system that actively regulates temperatures of at least one stream and includes a controller and treatment device for blood, according to embodiments of the disclosed subject matter in which fluid balancing is performed in a method and system like that of FIG. 2A and a partial feedforward method and system are used for temperature regulation. Referring to FIG. 3A, a temperature sensor 2161 is connected to the controller 202 and indicates the temperature of the fluid in treatment fluid line 201B that is applied to the treatment device 204. The temperature indication of the fluid applied to the treatment device 204 is feedback controlled to a target temperature estimated to be required for achieving the target blood return temperature rather than directly calculating the power required to obtain that temperature. Effectively this like setting a thermostat to regulate the power of the temperature regulator 206.

Figure 3B:
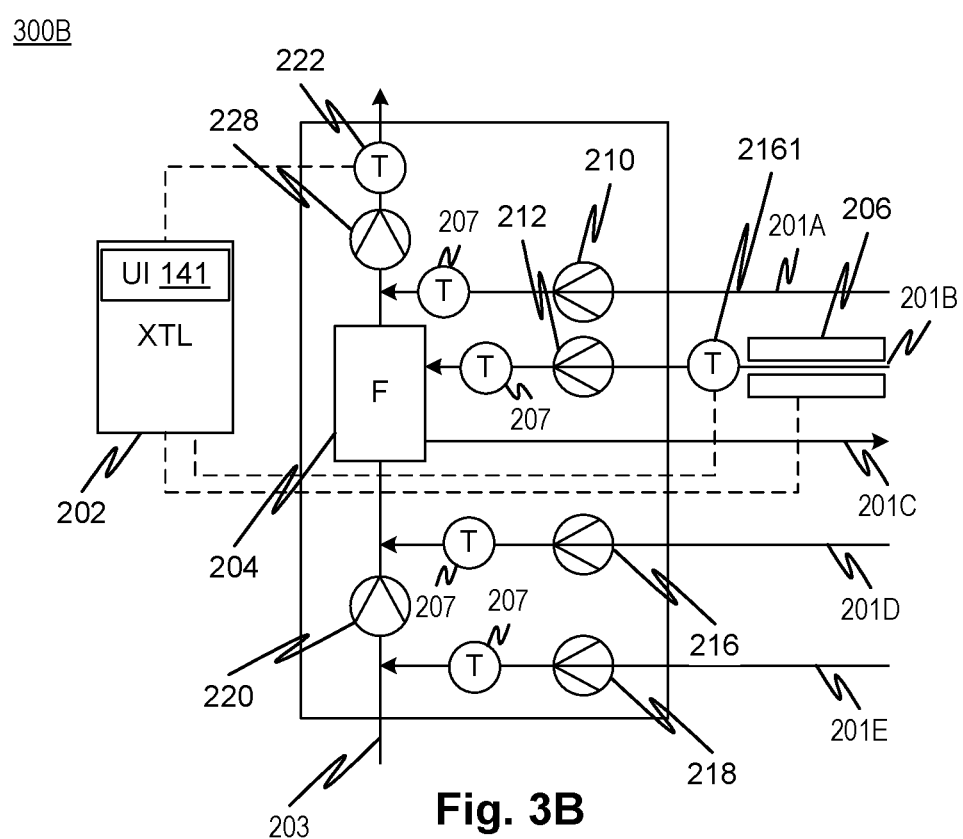
FIG. 3B shows a simplified schematic of a multiple treatment fluid stream system that actively regulates temperatures of at least one stream and includes a controller and treatment device for blood, according to embodiments of the disclosed subject matter in which fluid balancing is performed in the alternative method and system as in FIG. 2B and temperature regulation includes a feed-forward method and system as in FIG. 3A.

FIG. 3B shows a simplified schematic of a multiple treatment fluid stream system that actively regulates temperatures of at least one stream and includes a controller and treatment device for blood, according to embodiments of the disclosed subject matter in which fluid balancing is performed in the alternative method and system as in FIG. 2B and temperature regulation includes a thermostatic device of FIG. 3A.

Figure 5:
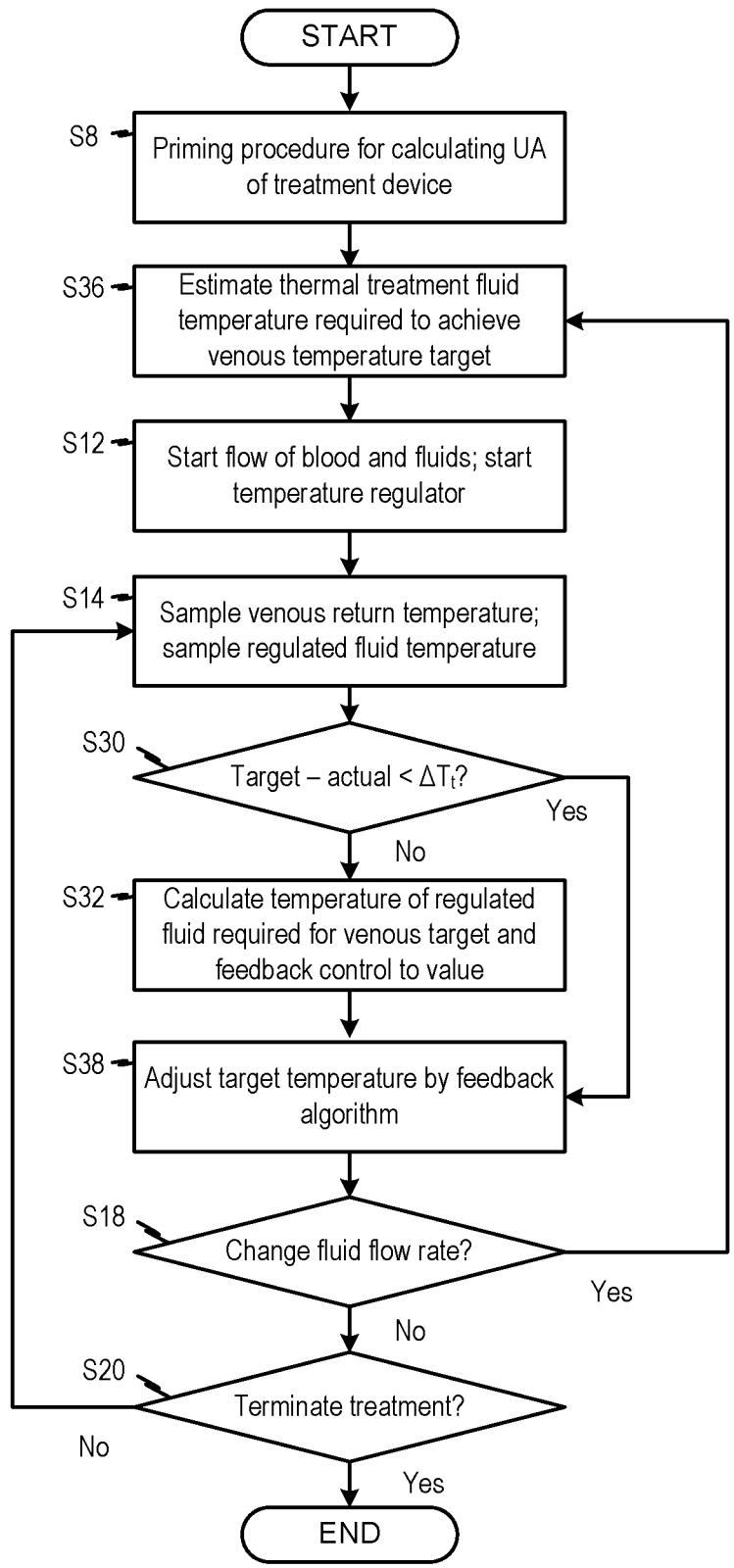
FIG. 5 shows a flow chart defining a controller-implemented method of regulating venous return temperature in the presence of multiple fluids that affect the temperature as shown in the systems of FIGS. 3A and 3B, according to embodiments of the disclosed subject matter.

FIG. 5 shows a flow chart defining a controller-implemented method of regulating venous return temperature in the presence of multiple fluids that affect the temperature as shown in the systems of FIGS. 3A and 3B, according to embodiments of the disclosed subject matter. Step S8 represents an example of a priming procedure which is illustrated in more detail in FIG. 6. The priming procedure calculates UA, which is the overall heat transfer coefficient, where U=heat transfer coefficient normalized by area (W/m$^2$K), and A is the area in m$^2$. The control flow proceeds as in the flow chart of FIG. 4 except that instead of estimating the power output of the temperature regulator 206, a target temperature of the fluid in treatment fluid line 201B and flowing into treatment device 204 is calculated and used by the controller to feedback-control the power of the temperature regulator 206 to achieve the target temperature of the fluid in treatment fluid line 201B responsively to the temperature indicated by temperature sensor 2161. This occurs at S36 in place of S10. The estimation may be done according to variety of methods implementable by a digital controller, for example as described above with reference to FIGS. 7 and 8. At S30, the controller determines whether the temperature of the target temperature of the fluid in treatment fluid line 201B is correct and if not, executes feedback control of the temperature regulator 206 at S32. If the blood return temperature is within the stored predefined range at S30, then control proceeds to S38, where the target temperature for of the fluid in treatment fluid line 201B is adjusted by a feedback algorithm and stored by the controller based on the sampled venous return temperature. In other respects, the method of FIG. 5 is the same as that of FIG. 4.

Figure 6:
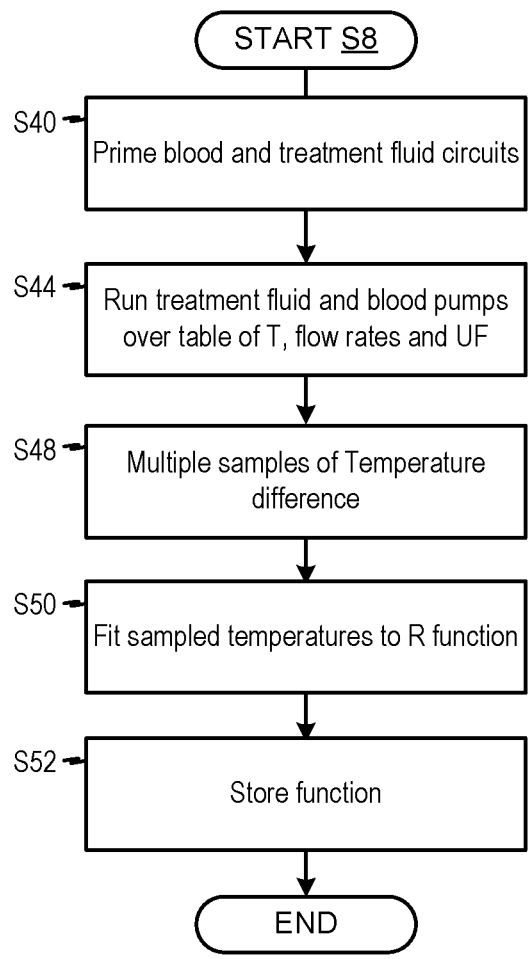
FIG. 6 shows a flow chart defining a controller-implemented method for obtaining a control input parameter during priming of a system and used in the methods of FIGS. 3A and 3B, according to embodiments of the disclosed subject matter.

FIG. 6 shows a flow chart defining a controller-implemented method for obtaining a control input parameter during priming of a system and used in the methods of FIGS. 3A and 3B, according to embodiments of the disclosed subject matter. Referring to FIG. 6, a look up table or function provides $(T_{F3}-T_{B,3})=F(UF, m_{F3}, m_{B,3})$ as described above. At S40, treatment fluid circuit including blood and treatment fluid portions is primed. The priming fluid in the treatment fluid circuit may serve as a model of blood. The configuration may include active cooling and heating of all fluids to permit any selected temperature of the blood and treatment fluids (which may also be represented by priming fluid). At S44, the fluids are circulated for an array of UF, $m_{F3}$, $m_{B,3}$ values and the delta values $T_{F3}-T_{B,3}$ recorded at S48 for each. The resulting set may be fitted to a look up table or function S50 which is stored S52 for use during treatment.

Figure 9A:
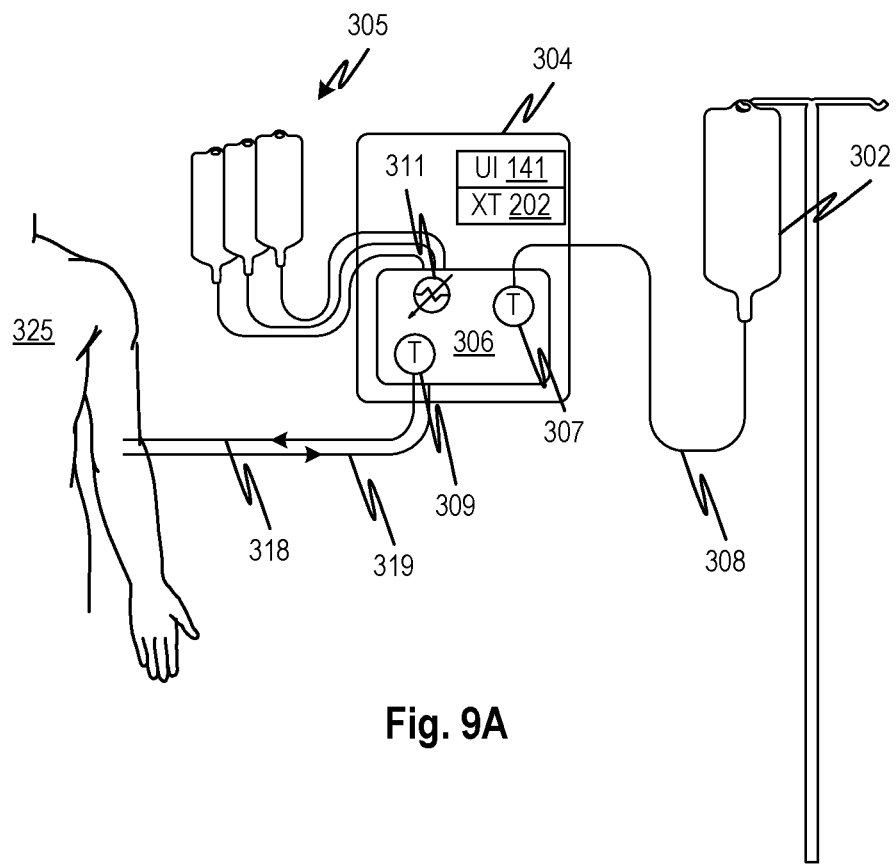
FIGS. 9A and 9B show systems that combine an external fluid source with a single or multiple-stream extracorporeal blood treatment device where the extracorporeal blood treatment device manages the patient body temperature by regulating the temperature of a subset of the streams that affect blood return temperature.
Figure 9B:
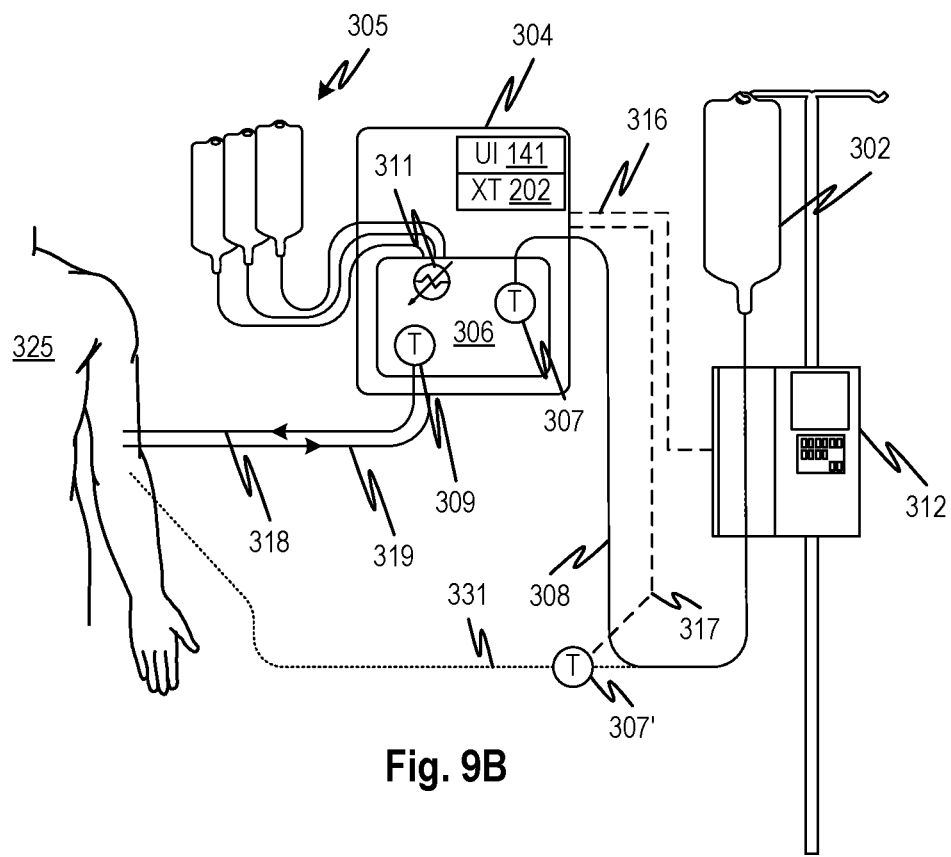

FIGS. 9A and 9B show systems in which a separate source 302 of intravenously-administered fluids is provided to a patient 325 through an IV line 308 at a time of treatment by a blood treatment machine 304. Normally, IV line 308 would be connected directly to the patient, as shown in FIG. 9B, connected to optional IV line 331. In the foregoing embodiments, a blood return temperature that is effective to regulate a patient body temperature is shown to be maintained by regulating the temperature of a treatment fluid that affects the blood return temperature. Referring now to FIG. 9A, a blood treatment machine 304 processes blood using one or more fluids 305. In the present embodiment, the blood treatment machine 304 consumes the one or more treatment fluids 305 to treat the patient 325. One of the treatment fluids may be consumed at a higher rate than the others, for example, dialysate or replacement fluid for hemofiltration. That one fluid alone, or in combination with a subset of multiple fluids 305 may be heated by a heater 311 to regulate the temperature of return blood carried by a venous line 318 to regulate the temperature of the patient 325. Blood is drawn from the patient 325 through arterial line 319 and returned to the patient 325 through the venous line 318 after being treated. The blood return temperature may be detected by a temperature sensor 309. Element 306 is a fluid circuit support structure with sensors and actuators.

In addition, the patient 325 core temperature may be detected from the arterial blood temperature by a suitable positioned temperature sensor like temperature sensor 309, in an embodiment. As described in International Patent Publication WO/2017/062923, a core temperature measurement may be made by varying the heat transfer dynamics of a blood circuit and fitting parameters of a blood circuit heat transfer configuration to measurements under the varied conditions. Then the input temperature of the patient core can be extracted from the model and a current temperature measurement remote from the patient core and optionally other measurements such as blood flow rate. In a principal application, a patient's body temperature is calculated responsively to a temperature of blood flowing through a blood circuit taken at an extracorporeal blood treatment component. Blood flows into an arterial line in an extracorporeal blood circuit through one or more devices such as a treatment device, and back to a patient. Body core temperature may be calculated from a measured arterial blood temperature using a sensor that is remote from the inlet. To do this, the temperature may be measured at multiple flow rates and temperature readings for each condition stored. Then these readings may be used with a thermal model of the system to calculate the inlet temperature. In an embodiment, the heat transfer rate is the same for two flow rate conditions. This gives two unknowns (the heat transfer rate) and two equations allowing the inlet temperature to be calculated from the remote temperature readings and the flow rates, which are known. In embodiments this initial estimate of the inlet temperature can be improved by using an initial guess, estimate, or measurement of the ambient temperature to recursively calculate an improved estimate of the inlet temperature which may be used again to improve it until converged. In other embodiments the unknown parameters of inlet temperature heat transfer rate (power units) may be calculated using a brute force optimization method such as an annealing algorithm or Monte Carlo method. The latter may be preferred where the fluid temperature is modeled as an exponential (decay), for example using log mean temperature difference (LMTD). In further embodiments, the ambient temperature may be estimated by fitting three temperatures and three flow rates as knowns to a thermal model of the flow system. Details of the core temperature measurement method that may be applied to the present embodiments are described in International Patent Publication WO/2017/062923.

The separate source 302 may be any type of intravenous fluid or medicament treatment fluid that transfers heat to the venous blood return through venous line 318 or which affect the temperature of a directly connected patient 325. Note that direct connection to the patient is not shown in FIG. 9A but a patient may be directly connected by a separate line 331 instead of through the blood treatment machine 304 as illustrated in both FIGS. 9A and 9B. Continuing to refer to FIG. 9A, the through the blood treatment machine 304 functions as an intravenous fluid pump by metering intravenous fluid from the separate source 302 using an internal pump (not shown) whose rate may be controlled by a user interface (not shown separately but it should be clear the through the blood treatment machine 304 of FIGS. 9A and 9B may be configured with a user interface 141 as described above in the disclosure of the embodiments of FIGS. 1 through 3B. Blood treatment machine 304 pumps intravenous fluid at a rate commanded through the user interface 141. The blood treatment machine 304 adjusts the temperature of one or more of the fluids 305 to achieve the control goal of a target core temperature of the patient 325 or a target blood return temperature. The intravenous fluid is admixed with blood in the same manner as described with respect to the replacement and other fluids of the foregoing embodiments. The temperature of the intravenous fluid is indicated by a temperature sensor 307. The blood treatment machine 304 controls the pump used to regulate the flow of intravenous fluid and therefore, control by the blood treatment machine 304 may be responsive to the temperature and flow rate of the intravenous fluid from the source 302 in the manner described above with regard to the other embodiments.

In the embodiment of FIG. 9B, a separate infusion pump 312 is controlled by its own user interface, but it sends indications of treatment parameters to the controller 202 of the blood treatment machine 304 by a signal link 316, for example a conductive cable or a wireless link. The temperature of the fluid may be detected directly by the blood treatment machine 304 using a temperature sensor 307. Since the blood treatment machine thus has access to the flow rate and temperature, the disclosed control method may be used to regulate the patient blood return temperature. Note that in the embodiments of FIGS. 9A and 9B, the intravenous fluid is assumed to be admixed with blood at a point upstream of the blood return temperature which is provided by the temperature sensor 309. In the alternative embodiment of FIG. 9B in which the intravenous fluid is infused through a separate line 331, the blood treatment machine may provide an external temperature sensor 307' that may be attached to the separate line 331 to apply a temperature signal to the blood treatment machine controller 202. The external temperature sensor 307' could be externally mounted or tethered to the treatment machine and provide a temperature signal via a wired or wireless link 317 to the treatment machine.

In any of the embodiments, including the embodiments defined by the claims, additional embodiments may be created by adding a feature in which the blood return temperature is controlled by negative feedback control loop responsively to the detected patient core temperature such that the control variable of blood return temperature is slaved to the patient core temperature. The patient core temperature may be estimated from the blood return temperature as discussed. The blood return temperature required to achieve a target core temperature may be calculated based on data representing a model of the patient's thermal regulation requirements that has been customized for the patient. The data may be improved over time based on a continuous detection of core temperature during a treatment. The blood return temperature may be slaved to the target core temperature as a feedback control loop. Thus, the control methods described above may be used to regulate a heater or cooler to adjust the treatment fluid temperature(s) to achieve a target blood return temperature (venous blood temperature) and an outer control loop may be implemented to adjust target blood return temperature to achieve a target core temperature. A net cooling or heating rate may be stored for the patient and used to establish an initial blood return temperature target at the beginning of a successive treatment. The net cooling or heating rate may be normalized by room temperature by entering the room temperature in the user interface 141 or by direct measurement of the room temperature. It may also be normalized by the time of the treatment, time of last meal, type of meal (e.g., high protein or low protein meal), or other factors that affect metabolic rate. Coefficients for each of these factors may be stored in a look up table (LUT) each of whose entries corresponds to a respective answer to a question or a measurement indication (or range thereof). For example, the room temperature ranges may be respective entries in the LUT. Protein level of the most recent meal may be divided into some number of levels, for example 3 corresponding to high protein, medium protein, or low protein. Other examples may be readily determined by the skilled designer and need not be elaborated herein.

According to embodiments, the disclosed subject matter includes apparatus for controlling flow in a fluid circuit. A treatment machine with flow regulators, a temperature regulator, and temperature sensors has a controller connected to control the flow regulators and receive signals from the temperature sensors to implement a therapeutic treatment by regulating the flow rates in each of multiple treatment fluid lines and in each of arterial and venous blood lines of a predefined fluid circuit connectable in operative engagement with the flow regulators, the temperature sensors, and the temperature regulator. The predefined fluid circuit is of a type in which the arterial and venous blood lines and at least some of the treatment fluid lines transfer heat and fluids between the treatment fluid lines and the arterial and venous blood lines. The controller is programmed to control the flow regulators to regulate respective flow rates in the treatment fluid lines and the arterial and venous blood lines to produce a predetermined difference between flows in the arterial and venous blood lines. The controller further is programmed to control the temperature regulator to exchange heat with a subset of the multiple fluid lines to achieve a predefined temperature in the venous blood line.

In variations of the foregoing embodiment or embodiments, the subset is a single one of the multiple treatment fluid lines. In further variations of the foregoing embodiments, the single one is a dialysate or replacement fluid line. In the temperature regulator includes a warmer. In further variations of the foregoing embodiments, the temperature sensors include a blood return temperature senor that indicates a blood return temperature and engages the venous blood line and a temperature-regulator sensor that engages the single one of the multiple treatment fluid lines. In further variations of the foregoing embodiments, the controller is programmed to ensure that a temperature of the fluid in the single one of the multiple treatment fluid lines remains below a predefined long term temperature at all times. In further variations of the foregoing embodiments, the controller is programmed to ensure that a temperature of the fluid in the single one of the multiple treatment fluid lines remains at, or below, a predefined long term temperature at all times and at, or below, below a predefined short term temperature for no longer than a predefined short term time interval, whereby blood is not exposed to fluid at temperatures above the long or short term temperatures at any time or for longer than the predefined short term time interval, respectively. In further variations of the foregoing embodiments, the temperature sensors include multiple treatment fluid temperature sensors that engage the multiple treatment fluid lines, respectively and wherein controller is programmed to control the temperature regulator responsively to temperatures indicated by the multiple treatment fluid sensors. In further variations of the foregoing embodiments, the controller is programmed to compensate for a combined effect of heating and/or cooling by fluid in the multiple treatment fluid lines on the blood return temperature. In further variations of the foregoing embodiments, the controller is programmed to ensure that a temperature of the fluid in the single one of the multiple treatment fluid lines remains at, or below, a predefined long term temperature at all times and at, or below, below a predefined short term temperature for no longer than a predefined short term time interval. In such further variations, the controller is programmed to compensate for a combined effect of heating and/or cooling by fluid in the multiple treatment fluid lines on the blood return temperature and the temperature of the fluid in the single one of the multiple treatment fluid lines.

According to embodiments, the disclosed subject matter includes a method of regulating a blood return temperature during a blood treatment. The method includes withdrawing blood from a living subject and simultaneously cooling and heating the blood by admixing of one or more of at least two treatment fluids, withdrawing fluid from the blood, and transferring heat between the blood and the one or more of the at least two treatment fluids. The method includes returning the blood to the living subject after the simultaneously heating and cooling and detecting a temperature of the returning blood. The method includes using the controller connected to receive a signal indicating the temperature of the returning blood and responsively thereto, regulating a rate of heat addition or withdrawal to or from one of the at least two treatment fluids by means of a temperature regulator controlled by the controller to achieve a predefined temperature of the returning blood.

In variations of the foregoing embodiments, the regulating a rate of heat addition or withdrawal is responsive to respective flow rates of the at least two treatment fluids. In further variations of the foregoing embodiments, the regulating a rate of heat addition or withdrawal is responsive to a combined effect of the simultaneously cooling and heating. In further variations of the foregoing embodiments, the regulating a rate of heat addition or withdrawal is responsive to is respective flow rates of the at least two treatment fluids. In further variations of the foregoing embodiments, the one of the at least two treatment fluids is a dialysate. In further variations of the foregoing embodiments, the one of the at least two has a higher flow rate than one or more others of the at least two. In further variations of the foregoing embodiments, the regulating a rate of heat addition or withdrawal includes detecting treatment fluid temperatures. In further variations of the foregoing embodiments, the regulating is responsive to respective temperatures of the at least two treatment fluids. In further variations of the foregoing embodiments, the regulating is responsive to respective flow rates of the at least two treatment fluids. In further variations of the foregoing embodiments, the regulating is responsive to respective flow rates and temperatures of the at least two treatment fluids.

According to additional embodiments, the disclosed subject matter includes a method of regulating blood return temperature in an extracorporeal blood treatment. The method includes actively regulating a fluid temperature regulator power output, using feedback control based on a blood return temperature signal, to control the temperature of a subset of multiple medicament streams the flow into, or contact, flowing blood. The method includes detecting a change in a flow rate or temperature of any one of the multiple medicament streams. The method includes resetting a rate of the fluid temperature regulator power output using feedforward control responsively to the detecting.

In variations of the foregoing embodiments, the method further includes reverting to the actively regulating using feedback control following the resetting. In further variations of the foregoing embodiments, the feedforward control includes estimating a heat transfer occurring in a blood treatment device. In further variations of the foregoing embodiments, the method includes an initial resetting prior to the actively regulating using feedback control at the beginning of a blood treatment.

In further variations of the foregoing embodiments, the detecting a change in a flow or temperature of any one of the multiple medicament streams includes detecting a change in a rate of ultrafiltration.

In further variations of the foregoing embodiments, the subset is one of the multiple medicament streams.

According to embodiments, the disclosed subject matter includes apparatus for controlling flow in a fluid circuit. A treatment machine, having an extracorporeal blood processing function. The treatment machine having pump actuators each engageable with a respective fluid line of to pump a respective one of two or more treatment fluids. The treatment machine having a fluid temperature regulator that includes a heater or cooler that can be engaged with a fluid circuit to apply heat to a subset of the two or more treatment fluids. The treatment machine has a controller with a venous temperature input that receives a blood return temperature signal indicating a temperature of blood returning to a patient, a core temperature input that receives a core temperature signal indicating a core temperature of a patient undergoing treatment, and treatment fluid temperature inputs that receive respective temperatures of the two or more treatment fluids. The controller is connected to the fluid temperature regulator to regulate a heating and/or cooling output of the fluid temperature regulator. The controller calculates and stores a target blood return temperature responsively to the core temperature, the controller is programmed to regulate the heating and/or cooling output responsively to the stored target blood return temperature by regulating the output of the fluid temperature regulator to minimize a difference between the target blood return temperature and a detected blood return temperature.

In further variations of the foregoing embodiments, the subset is a single one of the two or more treatment fluids. In further variations of the foregoing embodiments, a heating and/or cooling effect of fluid in the subset is generated by the temperature in the subset reaching equilibrium with the temperature of blood due to heat transfer of admixing.

According to embodiments, the disclosed subject matter includes a method of regulating a blood return temperature during a blood treatment. The method includes withdrawing blood from a living subject and simultaneously cooling and heating the blood by admixing of one or more of at least two treatment fluids, withdrawing fluid from the blood, and transferring heat between the blood and the one or more of the at least two treatment fluids. The method includes returning the blood to the living subject after the simultaneously heating and cooling and detecting a temperature of the returning blood. The method includes using the controller connected to receive a signal indicating the temperature of the returning blood and responsively thereto, regulating a rate of heat addition or withdrawal to, or from, a subset of the at least two treatment fluids by means of a temperature regulator controlled by the controller to achieve a predefined temperature of the returning blood without actively heating or cooling others (than the subset) of the at least two treatment fluids.

In further variations of the foregoing embodiments, the regulating a rate of heat addition or withdrawal is responsive to respective flow rates of the at least two treatment fluids. In further variations of the foregoing embodiments, the regulating a rate of heat addition or withdrawal is responsive to a combined effect of the simultaneously cooling and heating. In further variations of the foregoing embodiments, the regulating a rate of heat addition or withdrawal is responsive to is respective flow rates of the at least two treatment fluids. In further variations of the foregoing embodiments, the subset of the at least two treatment fluids includes dialysate. In further variations of the foregoing embodiments, the subset includes a one of the at least two that has a highest flow rate of all the at least two. In further variations of the foregoing embodiments, the regulating a rate of heat addition or withdrawal includes detecting treatment fluid temperatures. In further variations of the foregoing embodiments, the regulating is responsive to respective temperatures of the at least two treatment fluids. In further variations of the foregoing embodiments, the regulating is responsive to respective flow rates of the at least two treatment fluids. In further variations of the foregoing embodiments, the regulating is responsive to respective flow rates and temperatures of the at least two treatment fluids.

It will be appreciated that the modules, controllers, processes, systems, and sections described above can be implemented in hardware, hardware programmed by software, software instruction stored on a non-transitory computer readable medium or a combination of the above. For example, a method for balancing fluid flow can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers and especially digital controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, flow balancing devices, methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method of regulating blood return temperature in an extracorporeal blood treatment, comprising:
    actively regulating a fluid temperature regulator power output, using feedback control based on a blood return temperature signal, to control a temperature of a subset of multiple medicament streams that flow into, or contact, flowing blood;
    detecting a change in a flow rate or temperature of any one of the multiple medicament streams; and
    resetting a rate of the fluid temperature regulator power output using feedforward control responsively to said detecting.

2. The method of claim 1, further comprising reverting to said actively regulating using feedback control following said resetting.

3. The method of claim 1, wherein the feedforward control includes estimating a heat transfer occurring in a blood treatment device.

4. The method of claim 1, further comprising an initial resetting prior to said actively regulating using feedback control at a beginning of a blood treatment.

5. The method of claim 1, wherein said detecting a change in a flow or temperature of any one of the multiple medicament streams includes detecting a change in a rate of ultrafiltration.

6. The method of claim 1, wherein the subset is one of the multiple medicament streams.

* * * * *